Figure 1:
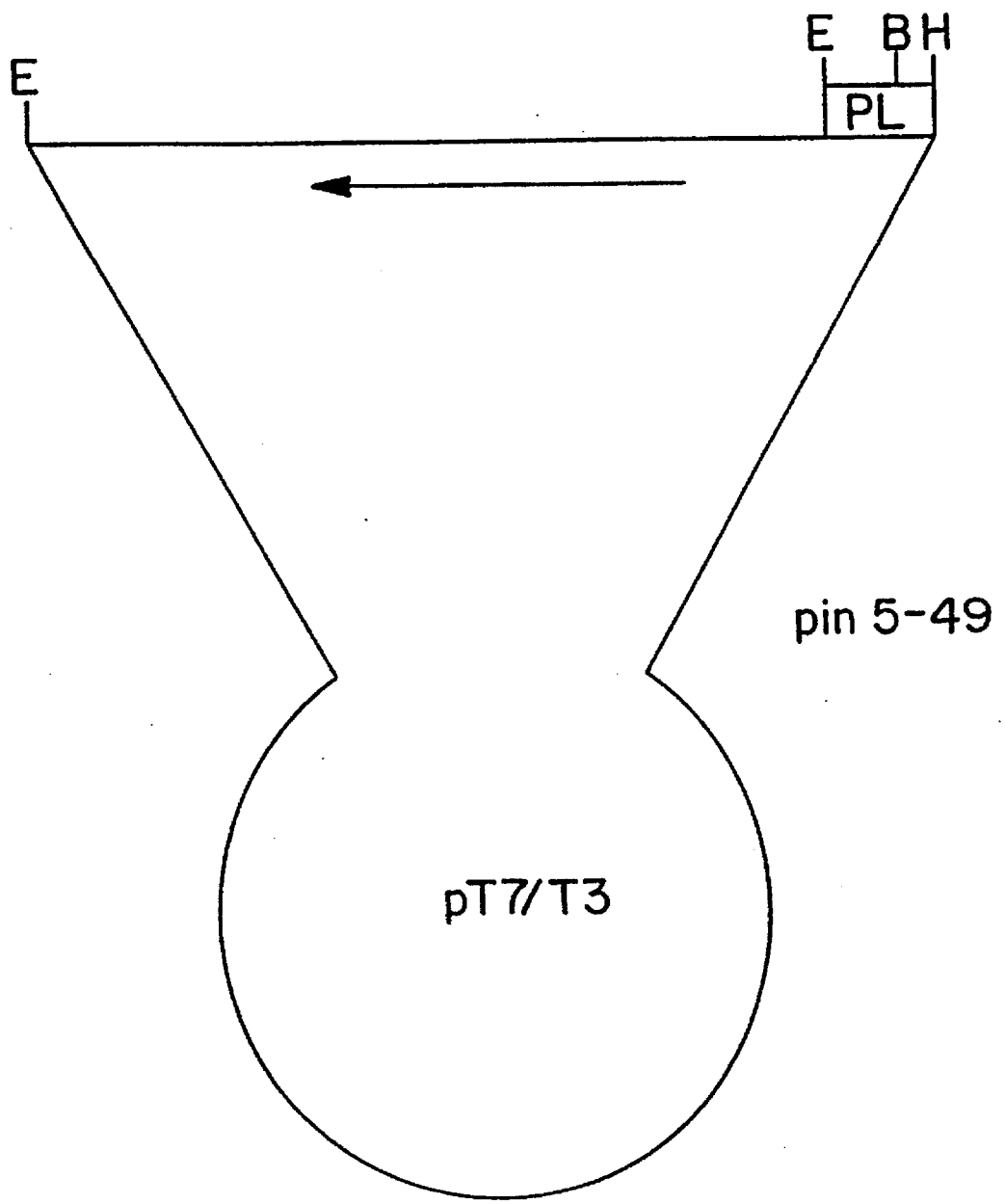

United States Patent [19]

Kindl et al.

[11] Patent Number: 5,589,621
[45] Date of Patent: Dec. 31, 1996

[54] PINOSYLVINE SYNTHASE GENES

[75] Inventors: Helmut Kindl, Marburg; Rüdiger Hain, Langenfeld; Hans-Jörg Reif, Cologne; Klaus Stenzel, Duesseldorf; Jürgen Thomzik, Langenfeld, all of Germany

[73] Assignee: Bayer Aktiengesellschaft, Leverkusen, Germany

[21] Appl. No.: 338,996

[22] Filed: Nov. 14, 1994

Related U.S. Application Data

[62] Division of Ser. No. 941,469, Sep. 8, 1992, Pat. No. 5,391,724.

[30] Foreign Application Priority Data

Sep. 18, 1991 [DE] Germany ............ 41 30 986.3

[51] Int. Cl.⁶ .............. A01H 4/00; C12N 5/14
[52] U.S. Cl. ............ 800/205; 435/240.4; 800/DIG. 23
[58] Field of Search .............. 800/205, DIG. 23; 435/240.4, 320.1, 172.3, 69.1; 536/23.2

[56] References Cited

FOREIGN PATENT DOCUMENTS 0309862  4/1989  European Pat. Off. .

OTHER PUBLICATIONS

1988, Pharmacia Catalogue, p. 14.
Potrykus. Jun. 1990, Bio/Technology 8:535–542.
Ou–Lee et al., 1986, PNAS USA 83:6815–6819.
Barton et al., 1987, Plant Physiol. 85:1103–1109.
Watson et al., 1987, Molecular Biology of the Gene, 4th ed., p. 313.
Jefferson et al., 1986, PNAS USA 83:8447–8451.
Schwekendiek et al., Apr. 1992, FEBS Lett. 301:41–44.
Schröder et al., 1988, Eur. J. Biochem. 172:161:169.
Schoeppner et al., 1979, FEBS Lett. 108:349–352.
Hain et al., 1990, Plant Mol. Biol. 15:325–335.
E. Jorgensen, Can. J. Bot., 39, pp. 1765–1772 (1961).
G. Billek, in Fortschritte der Chemie Organischer Naturstoffe, 22 (Zechmeister, L. ed.), Springer, Wien, pp. 115–152 (1964).
H. Kindl, in Biosynthesis and biodegradation of wood components (T. Higuchi, Ed.), Academic Press, New York, pp. 349–377 (1984).
R. Gehlert et al., Mol. Plant–Microbe Interactions, 3. pp. 444–449 (1990).
J. Ebel, Annu. Rev. Phytopathol., 24, pp. 235–264 (1989).
Biological Chemistry Hoppe–Seyler, The Official Organ of the Gesellschaft Für Biologische Chemie, Sep. 1991, vol. 372, No. 9, pp. 660–661.
Ann. Rev. Phytopathol., vol. 19, 1981, pp. 437–458.
Phytopathology, vol. 69, No. 10, 1979, pp. 1138–1143.

*Primary Examiner*—Che S. Chereskin
*Attorney, Agent, or Firm*—Sprung Horn Kramer & Woods

[57] ABSTRACT

New genes for pinosylvine synthase ("pinosylvine synthase genes") have been found, which can be incorporated into the hereditary factors (the genome) of plants that generate no pinosylvine or only inadequate pinosylvine, whereby an increased resistance of these plants to pests can be brought about. Also disclosed are vectors, host organisms, and plants transformed with the new pinosylvine synthase genes.

3 Claims, 1 Drawing Sheet

PINOSYLVINE SYNTHASE GENES

This is a division of application Ser. No. 07/941,469, filed on Sep. 8, 1992, now U.S. Pat. No. 5,391,724.

The present invention relates to new genes, isolated from plants, for pinosylvine synthase and to their use for the transformation of vectors, host organisms and plants and for generation of plants which have an increased resistance to pests.

3,5-Dihydroxy-stilbene, which occurs in plants and has a toxic action on pests, in particular fungi, bacteria and insects, and is therefore suitable for warding off these pests, is called pinosylvine. The capacity for synthesis of these substances by the plants is regarded as an important defence mechanism. Unfortunately, only few beneficial plants have the capacity to form pinosylvine or to generate it in an amount which imparts to them an adequate resistance to pests.

The use of stilbene synthase genes for generation of plants having an increased resistance to pests is already known from EP-A-0 309 862. A resveratrol synthase gene from peanut plants (Arachis hypogea) is described specifically in this publication.

New genes for pinosylvine synthase ("pinosylvine synthase genes") have now been found, which can be incorporated into the hereditary factors (the genome) of plants which generate no pinosylvine or only inadequate pinosylvine, whereby an increased resistance of these plants to pests can be brought about.

Surprisingly, the new pinosylvine synthase genes have considerably better resistances to pests in plants than the resveratrol synthase gene from peanut.

By pinosylvine synthase genes there are to be understood any nucleic acid (DNA) which, after transcription into RNA and translation into protein, causes the formation of an enzyme which has the properties of a pinosylvine synthase, this nucleic acid being isolated from its natural environment or integrated into a vector or contained as "foreign" DNA or as "additional" DNA in a prokaryotic or eukaryotic DNA.

By pinosylvine synthase genes there are also to be understood those pinosylvine synthase genes which still contain, at their start and/or end, DNA sequences which do not or do not substantially impede the function of the genes. These DNA sequences, which are also called "gene units", are formed, for example, by excision with restriction enzymes, since no cutting points are available for customary restriction enzymes exactly at the start and at the end of the gene. The pinosylvine synthase genes or the gene units can also carry on their ends those DNA sequences which are in each case appropriate for their handling (for example "linkers").

The pinosylvine synthase genes (or the gene units) can exist in the form in which they are contained in the genome of plants ("genomic" form, including sequences which do not encode pinosylvine synthase and/or do not have a regulatory action (such as introns)), or in a form which corresponds to the cDNA ("copy" DNA) obtainable via RNA with the aid of reverse transcriptase/polymerase (and no longer contains introns). The pinosylvine synthase genes can also be present in a partly or completely synthetic form. By synthetic genes there are also understood those which are formed by renewed joining of parts of natural genes.

DNA segments in the pinosylvine synthase genes according to the invention (or the gene units) can be replaced by other DNA segments or DNAs which have essentially the same action.

In the present connection, by "foreign" DNA there is to be understood that DNA which does not occur naturally in a certain prokaryotic or eukaryotic genome, but is taken up in this genome only by intervention by man. "Additional" DNA is intended to mean that DNA which, although it occurs naturally in the particular prokaryotic or eukaryotic genome, has been taken up in this genome in an additional amount by intervention by man. One or more copies of the "foreign" DNA or "additional" DNA can be incorporated, depending on requirements and on the nature of the case in question.

Pinosylvine synthase which is formed in plants or plant cells with the assistance of the pinosylvine synthase genes according to the invention (or the gene units) means any enzyme which acts like pinosylvine synthase and, in plants, increases their resistance to pests.

The preferred pinosylvine synthase genes according to the invention are characterised in that they hybridise with the cDNA sequence contained in the plasmid pin 5-49 or its components or with the cDNA sequence according to SEQ ID No: 1 or its components and encode pinosylvine synthase FIG. 1 represents the plasmid pin 5-49. The pinosylvine synthase cDNA lies on the EcoRI fragment about 1.3 kb in size. In FIG. 1, "E" denotes EcoRI; "B" denotes Bam HI; "H" denotes Hind III; and "PL" denotes polylinkers from the plasmid pT7/T3.

Pinosylvine synthase genes which are preferred according to the invention are the pinosylvine synthase genes which occur in pine trees (Pinus sp.), particularly preferably in Pinus sylvestris, and can be isolated from these.

The pinosylvine synthase gene, the part sequence of which is present in the form of the cDNA on the plasmid pin 5-49 (which is described below in more detail) and the DNA sequences which have essentially the same action are especially preferred as the pinosylvine synthase gene according to the invention.

The cDNA contained on the plasmid was isolated from Pinus sylvestris. It consists of a sequence about 1,300 base pairs long. A part sequence of 570 base pairs originates from the sequence protocol SEQ ID No: 1.

It has been found that the pinosylvine synthase genes which occur in plants (in particular pine trees and especially preferably Pinus sylvestris) have wide regions of DNA sequence homology. On the basis of the sequence homology, the pinosylvine synthase genes according to the invention can therefore be isolated from plants in a simple manner with the aid of the cDNA contained on the plasmid pin 5-49 or its components or the sequence information according to SEQ ID No: 1 in the customary manner using the known methods of molecular biology.

Possible plants from which pinosylvine synthase genes according to the invention can be isolated are practically all the monocotyledonous or dicotyledonous plants, preferably dicotyledonous plants, pine trees (Pinus sp.), and particularly preferably Pinus sylvestris, being mentioned by way of example and as preferred.

As already mentioned, pinosylvine synthase genes or the encoding region thereof which hybridise with the cDNA which lies on the plasmid pin 5-49 are preferred according to the invention. The gene or the encoding region of the gene can be obtained in the customary manner with the aid of the cDNA.

The *Escherichia coli* strain E. coli pin 5-49 contains the plasmid pin 5-49. This strain has been deposited at the Deutsche Sammlung von Mikroorganismen (DSM, German Collection of Microorganisms), Mascheroder Weg 1b, D-3300 Braunschweig, Federal Republic of Germany, in accordance with the conditions of the Budapest Treaty on the International Recognition of Deposition of Microorganisms for the purposes of Patent Proceedings (deposition date: 29th Aug. 1991). It has been given deposition number DSM 6689.

The present invention also relates to this strain and its mutants. The plasmid pin 5-49 deposited in this host can easily be obtained in the necessary amounts in the customary manner by multiplication of the strain and subsequent isolation of the plasmid.

Functionally complete genes, such as the pinosylvine synthase genes according to the invention, consist of a component which has a regulatory action (in particular a promoter) and the structural gene which encodes the protein pinosylvine synthase.

Both parts of the gene can be used independently of one another. It is thus possible to follow the component having a regulatory action by another DNA sequence (deviating from the pinosylvine synthase gene) which is to be expressed after incorporation into the plant genome. Since only relatively few isolated promoters which can display their action in plants or plant parts are known, the promoters of the pinosylvine synthase genes, to which the present invention likewise relates, are useful aids in the generation of transformed plants or plant cells.

It is also possible to precede the pinosylvine synthase structural genes by a "foreign" component having a regulatory action. This could be advantageous if only certain (for example endogenous to the plant) genes having a regulatory action can have a sufficient action in certain plants. The pinosylvine synthase structural genes are therefore useful units which can be used independently and, as already mentioned, the present invention also relates to them. The pinosylvine synthase genes according to the invention can be separated into the components having a regulatory action and the structural genes by the customary methods. It is also possible to combine components of different naturally occurring pinosylvine synthase genes to give new functional "synthetic" genes. The complete natural pinosylvine synthase genes according to the invention (or the gene units) are preferably used.

It is possible, with the aid of customary methods, to incorporate the pinosylvine synthase genes (or the gene units) or components thereof one or several times (for example tandem arrangement), preferably once, into any desired prokaryotic (preferably bacterial) or eukaryotic (preferably plant) DNA as "foreign" or "additional" DNA. Thus, for example, the protein encoding DNA can be provided with regulatory sequences and incorporated into plants. The present invention relates to the recombinant DNA "modified" in this way, which can be used, for example, for the transformation of plants or plant cells and is contained in plants or plant cells after the transformation.

The pinosylvine synthase genes (or the gene units) and/or their components and the recombinant DNA can be contained, as "foreign" or "additional" DNA in vectors (in particular plasmids, cosmids or phages), in transformed microorganisms (preferably bacteria, in particular Gram-negative bacteria, such as *E. coli*) and in transformed plant cells and plants or in the DNA thereof. The present invention relates to such vectors, transformed microorganisms (which can also contain these vectors) and the transformed plant cells and plants and DNA thereof.

As already indicated, according to the invention the pinosylvine synthase genes (or the gene units) are incorporated once or several times (at the same or different points of the genome) into the natural plant genome, it also being possible for different genes to be combined with one another. In the case of plants which already have the capacity for pinosylvine synthase synthesis, the incorporation of one or more pinosylvine synthase genes according to the invention can lead to considerably improved resistance properties. In the case of plants which contain no pinosylvine synthase genes, an increased resistance to pests is likewise achieved by incorporation of such genes. If appropriate, only the structural genes according to the invention are used, these being preceded by any regulatory DNA element which may have been isolated from the particular plant.

The increased resistance of the transformed plant cells and plants according to the invention is of importance for agriculture and forests and for cultivation of ornamental plants, cultivation of medicinal plants and plant breeding. It is also advantageous in the culture of plant cells, for example for the production of pharmaceutically usable substances, to have available plant cells which have increased resistances to attack by microbial pests, in particular fungi.

The present invention thus also relates to a process for the preparation of transgenic plant cells (including protoplasts) and plants (including plant parts and seeds) having an increased resistance to pests, which is characterised in that (a) one or more pinosylvine synthase genes (or gene units) and/or components of the pinosylvine synthase genes (or of the gene units) and/or recombinant DNA according to the invention are inserted into the genome of plant cells (including protoplasts), and if appropriate (b) complete transformed plants are regenerated from the transformed plant cells (including protoplasts) and if appropriate propagated, and if appropriate (c) the desired plant parts (including seeds) are obtained from the resulting transgenic plants of the parent generation or further generations obtained therefrom.

Process steps (a), (b) and (c) can be carried out in the customary manner by known processes and methods.

The present invention also relates to transgenic plant cells (including protoplasts) and plants (including plant parts and seeds) which contain one or more pinosylvine synthase genes (or gene units) and/or components of the pinosylvine synthase genes (or of the gene units) as "foreign" or "additional" DNA, and to those transformed plant cells and plants which are obtainable by the above processes.

The present invention also relates to the:

(a) use of the pinosylvine synthase genes (or of the gene units) and/or their components and/or the recombinant DNA according to the invention and/or the recombinant vectors according to the invention and/or the transformed microorganisms according to the invention for the transformation of plant cells (including protoplasts) and plants (including plant parts and seeds), the (b) use of the transgenic plant cells (including protoplasts) and plants (including plant parts and seeds) according to the invention for the generation of propagation material and for the generation of new plants and propagation material thereof, the (c) use of the pinosylvine synthase genes according to the invention (or of the gene units) and/or their components and/or the recombinant DNA according to the invention for combating pests and the (d) use of the cDNA contained on the plasmid pin 5-49 or its components and of the DNA sequences corresponding to the sequence information according to sequence protocol SEQ ID NO:1 for isolation of pinosylvine synthase genes or components thereof from plants and for the determination of pinosylvine synthase genes in plants and (generally) in the generation of transgenic plant cells (including protoplasts) and plants (including plant parts and seeds).

There are a number of different methods available for inserting the pinosylvine synthase genes or the gene units or their components into the genetic material of plants or plant cells as "foreign" or "additional" DNA. The gene transfer can be carried out by the generally customary known methods, the expert being able to determine without difficulty the particular method suitable.

The Ti plasmid from *Agrobacterium tumefaciens* is available as a particularly favorable and widely applicable vector for the transfer of foreign DNA into genomes of dicotyledonous and monocotyledonous plants. The genetic material which encodes pinosylvine synthase is inserted into the T-DNA of suitable Ti plasmids together with regulatory DNA sequences (for example Zambryski et al. 1983) and transferred by infection of the plants, infection of plant parts or plant tissues, such as, for example, of leaves, stems, hypocotyls, cotyledons, meristems and tissues issuing therefrom, such as, for example, secondary embryos and calli, or by coculture of protoplasts with *Agrobacterium tumefaciens*.

An alternative is the incubation of purified DNA which contains the desired gene in plant protoplasts (for example Hain et al., 1985; Krens et al., 1982; Paszkowski et al., 1984) in the presence of polycations or calcium salts and polyethylene glycol.

The DNA uptake can also additionally be promoted by an electrical field (electroporation) (for example Fromm et al., 1986).

The DNA can also be introduced in a known manner via plant pollen, by "shooting" the pollen with physically accelerated particles which carry the DNA (compare EP-A 0,270, 356).

The plants are regenerated in a known manner with the aid of suitable nutrient media (for example Nagy and Maliga 1976).

In a preferred embodiment of the process according to the invention (in accordance with the method from EP-A 116, 718), the genes or gene units which, complementary to the cDNA from pin 5-49, are present in the genome of Pinus, are cloned in isolated form into a suitable intermediate *E. coli* vector, for example pGV700 or pGV710 (compare EP-A-116,718), or preferably derivatives thereof, which additionally contain a reporter gene, such as, for example, nptII (Herrera-Estrella et al. 1983) or hpt (Van den Elzen et al 1986).

The plasmid constructed in this way is transferred by customary methods (for example Van Haute et al. 1983) to *Agrobacterium tumefaciens*, which contains, for example, pGV 3850 or derivatives thereof (Zambryski et al. 1983). Alternatively, the pinosylvine synthase gene unit can be cloned in a binary vector, for example pCV001 or pCV002 (for example Koncz and Schell 1986) and transferred into a suitable Agrobacterium strain as described above (Koncz and Schell 1986). The resulting Agrobacterium strain which contains the pinosylvine synthase genes or gene units in a form which can be transferred to plants is subsequently used for the plant transformation.

In another preferred embodiment, the pinosylvine synthase gene units isolated, if appropriate together with another plasmid which contains a reporter gene for plant cells, for example for kanamycin resistance (for example Herrera-Estrella et al. 1983) or a hygromycin resistance (van den Elzen, 1986), preferably pLGV neo 2103 (Hain et al. 1985), pMON 129 (Fraley R. T. et al., Proc. National Acad. Sci. USA 80, 4803 (1983), pAK 1003, pAK 2004 (Velten J. et al., EMBO Journ. Vol. 3, 2723 (1984) or pGSST neo 3 (pGSST3) (EP-A-189,707), are transferred to plant protoplasts in the customary manner by direct gene transfer (for example Hain et al. 1985). In this case, the plasmid or plasmids can be present in circular form, but preferably in linear form. If a plasmid with a reporter gene is used, kanamycin-resistant protoplasts are then checked for expression of pinosylvine synthase. Otherwise (without a reporter gene), the resulting calli are checked for expression of the pinosylvine synthase gene or genes (screening by customary methods).

Transformed (transgenic) plants or plant cells are generated by the known methods, for example by leaf disc transformation (for example Horsch et al. 1985) by coculture of regenerating plant protoplasts or cell cultures with *Agrobacterium tumefaciens* (for example Marton et al. 1979, Hain et al. 1985) or by direct DNA transfection. Resulting transformed plants are detected either by selection for expression of the reporter gene, for example by phosphorylation of kanamycin sulphate in vitro (Reiss et al. 1984; Schreier et al. 1985) or by the expression of nopaline synthase (according to Aerts et al. 1983) or pinosylvine synthase by Northern blot analysis and Western blot analysis. The pinosylvine synthase and the stilbenes can also be detected in a known manner with the aid of specific antibodies in transformed plants. Pinosylvine synthase can also be detected by an enzyme activity test (Gehlert et al., 1990).

Culture of the transformed plant cells and regeneration to give complete plants are carried out by the generally customary methods with the aid of the particular suitable nutrient media.

Both the transformed plant cells and the transformed plants which contain the pinosylvine synthase genes according to the invention (or the gene units) and to which the present invention relates exhibit a considerably higher resistance to pests, in particular phytopathogenic fungi.

In connection with the present invention, the term "plants" denotes both complete plants and also parts of plants, such as leaves, seeds, tubers, cuttings and the like. "Plant cells" include protoplasts, cell lines, plant calli and the like. "Propagation material" denotes plants and plant cells which can be used for propagation of the transformed plants and plant cells, and the present invention thus also relates to this material.

In the present connection, the term "DNA sequences having essentially the same action" means that the invention also relates to those modifications in which the function of the pinosylvine synthase genes and their components is not impaired such that pinosylvine synthase is no longer formed or the regulatory gene component is no longer active. Corresponding modifications can be made by replacement, addition and/or removal of DNA sections, individual codons and/or individual nucleic acids.

In the case of microorganisms which can be used according to the invention, "mutants" denote those modified microorganisms which still have the features essential for implementation of the invention, and in particular contain the plasmid pin 5-49.

The plants which can be given resistance or an increased resistance to pests by incorporation (transformation) of the pinosylvine synthase genes according to the invention (or the gene units) include practically all plants. There is of course a particular need for generating resistance in crop plants, such as forest plants, for example spruce, fir, Douglas fir, pine, larch, beech and oak, as well as plants which supply foodstuffs and raw materials, for example cereals (in particular wheat, rye, barley, oats, millet, rice and corn), potatoes, leguminous plants (such as pulses and in particular alfalfa and soybean), vegetables (in particular cabbage varieties and tomatoes), fruit (in particular apples, pears, cherries, grapes, citrus fruits, pineapples and bananas), oil palms, tea, cocoa and coffee shrubs, tobacco, sisal and cotton, and in the case of medicinal plants, such as Rauwolfia and Digitalis. Potatoes, tomatoes and leguminous plants may be mentioned particularly preferably. The pinosylvine synthase genes according to the invention are preferably incorporated into the genome of plants as "foreign" DNA.

As pests against which resistances or increased resistances can be achieved with the aid of the pinosylvine synthase genes according to the invention there may be mentioned animal pests, such as insects, mites and nematodes, as well as microbial pests, such as phytopathogenic fungi, bacteria and viruses. Microbial pests, in particular phytopathogenic fungi, are particularly singled out.

The harmful insects include, in particular, insects of the orders:

Orthoptera, Dermaptera, Isoptera, Thysanoptera, Heteroptera, Homoptera, Lepidoptera, Coleoptera, Hymenoptera and Diptera.

The harmful mites include, in particular: Tarsonemus spp., Panonychus spp. and Tetranychus spp.

The harmful nematodes include, in particular: Pratylenchus spp., Heterodera spp. and Meloidogyne spp.

The microbial pests include, in particular, the phytopathogenic fungi:

Plasmodiophoromycetes, Oomycetes, Chytridiomycetes, Zygomycetes, Ascomycetes, Basidiomycetes and Deuteromycetes.

The phytopathogenic bacteria include, in particular, the Pseudomonadaceae, Rhizobiaceae, Enterobacteriaceae, Corynebacteriaceae and Streptomycetaceae.

The virus diseases include, in particular, mosaic, dwarfing and yellowing viroses.

Some causative organisms of viral, fungal and bacterial diseases which come under the generic names listed above may be mentioned as examples, but not by way of limitation:

barley yellow dwarf virus (BYDV), potato virus Y (PVY), cucumber mosaic virus (CMV), watermelon mosaic virus (WMV), Tristeza virus, tobacco mosaic virus (TMV), tobacco necrosis virus (TNV), beet necrotic yellow vein virus (BNYVV), rhizomania virus.

Xanthomonas species, such as, for example, Xanthomonas campestris pv. oryzae; Pseudomonas species, such as, for example, *Pseudomonas syringae* pv. lachrymans; Erwinia species, such as, for example, *Erwinia amylovora*; Pythium species, such as, for example, *Pythium ultimum*; Phytophthora species, such as, for example, *Phytophthora infestans*;

Pseudoperonospora species, such as, for example, *Pseudoperonospora humuli* or *Pseudoperonospora cubense*; Plasmopara species, such as, for example, *Plasmopara viticola*; Peronospora species, such as, for example, *Peronospora pisi* or *P. brassicae*;

Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species such as, for example, *Puccinia recondita*; Tilletia species, such as, for example, *Tilletia caries*; Ustilago species, such as, for example *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*;

Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae*; and Pseudocercosporella species, such as, for example, *Pseudocercosporella herpotrichoides*. *Helminthosporium carbonum* may furthermore be mentioned.

The present invention shall be illustrated in more detail with the aid of the following embodiment examples:

1. Isolation of the Gene for Pinosylvine Synthase from Pinus

Plants and cell cultures from Pinus (*Pinus sylvestris*) contain the genes for pinosylvine synthase which cause the formation of pinosylvine synthase (size of the protein 45 00 D; reaction with specific antiserum) (Gehlert et al. 1990).

The known processes and methods of molecular biology such as are described in detail, for example, in the following handbook were used in the isolation of the pinosylvine synthase genes: Sambrook, J., Fritsch, E. F., Maniatis, T.: Molecular Cloning: A Laboratory Manual; Cold Spring Harbor Laboratory, Second Edition 1989.

A "gene library" for Pinus is first established: genomic DNA from enriched cell nuclei (Bedbrook, J., Plant Molecular Biology Newsletter 2, 24, 1981) is cut with the restriction enzyme NdeII such that DNA fragments having an average length of about 12,000 nucleotide pairs are formed. These fragments are cloned into the BamHI site of the lambda phage EMBL4 (Frischauf et al., J. Mol. Biol. 170, 827–842, 1983), and the phages are multiplied in *E. coli*. The phage population in its entirety contains, cloned in part fragments, the total genomic DNA of the Pinus-cells, and therefore also the genes for pinosylvine synthases (multigene family).

The genes for pinosylvine synthase, their mRNA and the pinosylvine synthase cDNA each contain the same nucleic acid sequences, since they can be derived from one another (gene→mRNA→cDNA). This means that the genes for pinosylvine synthase can be identified by specific hybridisation with the particular pinosylvine synthase cDNA or with specific oligonucleotides. Using this procedure genomic phage clones for pinosylvine synthase have been identified, transferred to tobacco and found to direct the synthesis of pinosylvine in the heterologous plants. The transgenic plants displayed an increased resistance to plant pathogens. The phages with the genes are identified by hybridisation, and then isolated and multiplied. The genomic DNA from Pinus cloned in this phages is mapped further by analysis with various restriction enzymes, and the position of the pinosylvine synthase genes is determined by further hybridisation experiments with cDNA sequences or synthetic oligonucleotides. Finally, the gene units are cut out of the phage by digestion with restriction enzymes, cloned in the correspondingly cut plasmid vector pUC18 (Gibco-BRLGmbH, Eggenstein, Federal Republic of Germany) and multiplied as recombinant plasmids.

2. Description of the Plasmid Pin 5-49 (Compare FIG. 1

The plasmid consists of two components:
(i) cDNA (part sequence) of pinosylvine synthase: the cDNA which has been inserted into the plasmid pT7/T3 is 1.3 kb long and can be cut out of the plasmid pin 5-49 with EcoRI.
(ii) Vector plasmid: the cDNA is cloned in the vector pT7/T3 (Pharmacia LKB GmbH, Freiburg Federal Republic of Germany). The size of the vector is 2800 nucleotide pairs. It carries the gene for ampicillin resistance, that is to say *E. coli* cells with this plasmid grow in nutrient media which contain the antibiotic ampicillin. Ori: designation for sequences which are necessary for multiplication of the plasmid in *E. coli*.

The plasmid pin 5-49 carries a gene for ampicillin resistance and contains the EcoRI fragment described above, of about 1.3 kb, as pinosylvine synthase cDNA. It can be multiplied in the customary manner in *E. coli* cells which contain pin 5-49 (*E. coli* pin 5-49).

Preferred nutrient medium for *E. coli* cells (for example JA221, Nakamura, K., Inouye, M., EMBO J. 1, 771–775, 1982) which contain pin 5-49 (*E. coli* pin 5-49):

| | |
|---|---|
| Bacto-Peptone* | 10 g |
| yeast extract | 5 g |
| NaCl | 5 g |
| agar | 20 g |
| $H_2O$ | 1 l |
| pH 7.5 | |
| Fermentation: 37° C., aerobic | |

*(Bacto is a trademark of DIFCO Lab. Detroit, USA).

3. Transformation of Tobacco a) Culture of tobacco shoots and isolation of tobacco protoplasts:

*Nicotiana tabacum* (Petit Havana SR1) is propagated as a sterile shoot culture on hormone-free LS medium (Linsmaier and Skoog 1965). Shoot sections are transferred to fresh LS medium at intervals of about 6–8 weeks. The shoot cultures are kept in 12 hours of light (1000–3000 lux) in a culture room at 24°–26° C.

For the isolation of leaf protoplasts, about 2 g of leaves (about 3–5 cm long) are cut into small pieces (0.5 cm×1 cm) with a fresh razor blade. The leaf material is incubated in 20 ml of enzyme solution consisting of K3 medium (Nagy and Maliga 1976), 0.4M sucrose, pH 5.6, 2% of Zellulase R10 (Serva) and 0.5% of Macerozym R10 (Serra) at room temperature for 14–16 hours. The protoplasts are then separated from cell residues by filtration over a 0.30 mm and 0.1 mm steel sieve. The filtrate is centrifuged at 100×g for 10 minutes. During this centrifugation, intact protoplasts float and collect in a band at the top margin of the enzyme solution. The pellet of cell residues and the enzyme solution are suctioned off with a glass capillary. The prepurified protoplasts are made up to 10 ml with fresh K3 medium (0.4M sucrose as an osmotic agent) and floated again. The washing medium is suctioned off and the protoplasts are diluted to $1-2\times10^5$/ml for culture or subsequent infection with Agrobacteria (coculture). The protoplast concentration is determined in a counting chamber.

b) Transformation of regenerating tobacco protoplasts by coculture with *Agrobacterium tumefaciens*:

The method of Marton et al. 1979 is used below, with minor modifications. The protoplasts are isolated as described and incubated in a density of $1-2\times10^5$/ml in K3 medium (0.4M sucrose, 0.1 mg/l of NAA, 0.2 ml in K3 medium (0.4M sucrose, 0.1 mg/l of NAA, 0.2 mg of kinetin) for 2 days in the dark and one to two days under weak light (500 lux) at 26° C. As soon as the first divisions of the protoplasts occur, 30 µl of an Agrobacterium suspension in minimal A (Am) medium (density about $10^9$ Agrobacteria/ml) are added to 3 ml of regenerating protoplasts. The duration of the coculture is 3–4 days at 20° C. in the dark. The tobacco cells are then introduced into 12 ml centrifuge tubes, diluted to 10 ml with seawater (600 mOsm/kg) and pelleted at 60×g for 10 minutes. This washing operation is repeated a further 1–2 times in order to remove the majority of the Agrobacteria. The cell suspension is cultured in a density of $5\times10^4$/ml in K3 medium (0.3M sucrose) with 1 mg/l of NAA (naphthyl-1-acetic acid), 0.2 mg/l of kinetin and 500 mg/l of the cephalosporin antibiotic cefotaxime. The cell suspension is diluted with fresh K3 medium every week and the osmotic value of the medium is reduced gradually by 0.05M sucrose (about 60 mOsm/kg) per week. Selection with kanamycin (100 mg/l of kanamycin sulphate (Sigma), 660 mg/g of active km) is started 2–3 weeks after the coculture in an agarose "bead type culture" (Shillito et al. 1983). Kanamycin-resistant colonies can be distinguished from the background of retarded colonies 3–4 weeks after the start of the selection.

c) Direct transformation of tobacco protoplasts with DNA. Calcium nitrate-PEG transformation.

About $10^6$ protoplasts in 180 µl of K3 medium are carefully mixed in a Petri dish with 20 µl of aqueous DNA solution which contains 0.5 µg/µl of plasmid carrying the genomic pinosylvine synthase gene and 0.5 µg/µl of pLGV neo 2103 (Hain et al. 1985). 200 µl of fusion solution (0.1M calcium nitrate, 0.45M mannitol, 25% of polyethylene glycol (PEG 6000), pH 9) are then carefully added. After 15 minutes, 5 ml of washing solution (0.275M calcium nitrate, pH 6) are added, and after a further 5 minutes, the protoplasts are transferred into a centrifuge tube and pelleted at 60×g. The pellet is taken up in a small amount of K3 medium and cultured as described in the next section. Alternatively, the protoplasts can be transformed as described by Hain et al. 1985.

The transformation can also be carried out without the addition of the 0.5 µg/µl of pLGV neo 2103. Since no reporter gene is used in this case, the resulting calli are checked for the presence of the pinosylvine synthase gene unit with the aid of a dot blot hybridisation. The cDNA sequence from pin 5-49 can be used as the hybridisation sample. Other detection methods, such as a test with antibodies or determination of a fungus resistance, can of course also be used.

d) Culture of the protoplasts incubated with DNA and selection of kanamycin-resistant calli:

A modified "bead type culture" technique (Shillito et al. 1983) is used for the culture and selection of kanamycin-resistant colonies described below. One week after treatment of the protoplasts with DNA (compare c), 3 ml of the cell suspension are mixed with 3 ml of K3 medium (0.3M sucrose+hormones; 1.2% (Seaplaque) of LMT agarose, Marine Colloids) in 5 cm Petri dishes. For this purpose, the agarose is autoclaved in the dry state and, after addition of K3 medium, is boiled up briefly in an microwave oven. After the agarose has solidified, the agarose discs ("beads") are transferred into 10 cm Petri dishes with the embedded tobacco microcalli for further culture and selection, and in each case 10 ml of K3 medium (0.3M sucrose, 1 mg/l of NAA, 0.2 mg/l of kinetin) and 100 mg/l of kanamycin sulphate (Sigma) are added. The liquid medium is changed every week. During this procedure, the osmotic value of the medium is reduced in stages.

The replacement medium (K3+km) is reduced by 0.05M sucrose (about 60 mOsm) per week.

Timetable of the selection of kanamycin-resistant tobacco colonies after DNA transformation:

| A | 0.4 M ES | 0.3 M | 0.25 M | 0.20 M | 0.15 M K | 0.10 M | sucrose in the liquid medium |
|---|---|---|---|---|---|---|---|
| DNA | 1 | 2 | 3 | 4 | 5 | | 6 weeks after |

Uptake
(K3 medium 1 mg of NAA, 0.2 mg of kinetin)
A = DNA uptake
E = embedding in agarose
S = selection with kanamycin (100 mg/l of kanamycin sulphate)
K = kanamycin-resistant colonies can be clearly distinguished from the background e) Regeneration of kanamycin-resistant plants:

As soon as the kanamycin-resistant colonies have reached a diameter of about 0.5 cm, half of them are placed on regeneration medium (LS medium, 2% of sucrose, 0.5 mg/l of benzylaminopurine BAP) and kept in the culture room in 12 h of light (3000–5000 lux) at 24° C. The other half are propagated as a callus culture on LS medium with 1 mg/l of NAA, 0.2 mg/l of kinetin, 0.1 mg/l of BAP and 100 mg/l of kanamydin sulphate. When the regenerated shoots are about 1 cm in size, they are cut off and placed on ½ LS medium (1% of sucrose, 0.8% of agar), without growth regulators, for rooting. The shoots are rooted on ½ MS medium with 100 mg/l of kanamycin sulphate and later transferred into soil.

f) Tranformation of leaf discs by *Agrobacterium tumefaciens*

For transformation of leaf discs (Horsch et al. 1985), leaves about 2–3 cm long from sterile shoot cultures are stamped into discs of 1 cm diameter and incubated with a suspension of appropriate Agrobacteria (about $10^9$/ml) (compare b) in Am medium, see below) for about 5 minutes. The infected pieces of leaf are kept on MS medium (see below) without hormones for 3–4 days at about 24° C. During this period, Agrobacterium grows over the pieces of leaf. The pieces of leaf are then washed in MS medium (0.5 mg/ml of BAP, 0.1 mg/ml of NAA) and placed on the same medium (0.8% of agar) with 500 µg/ml of cefotaxime and 100 µg/ml of kanamycin sulphate (Sigma). The medium should be renewed after two weeks. Transformed shoots are visible after a further 2–3 weeks. The regeneration of shoots should also be carried out in parallel without pressure of selection. The regenerated shoots must then be tested for transformation by biological tests, for example for nopaline synthase or pinosylvine synthase activity. 1–10% of transformed shoots are obtained in this manner.

Biochemical Detection Methods of Transformation

Detection of nopaline in plant tissues:

Nopaline is detected as follows, as described by Otten and Schilperoort (1978) and Aerts et al. (1979). 50 mg of plant material (callus or pieces of leaf) are incubated overnight in LS medium with 0.1M arginine at room temperature in an Eppendorf vessel. The plant material is then spotted onto absorbent paper, homogenised with a glass rod in a fresh Eppendorf centrifuge vessel and centrifuged in an Eppendorf centrifuge for 2 minutes. 2 µl of the supernatant are transferred in a punctiform manner onto a paper suitable for electrophoresis (Whatman 3 MM paper) (20×40 cm) and dried. The paper is impregnated with the mobile phase (5% of formic acid, 15% of acetic acid, 80% of $H_2O$, pH 1.8) and subjected to electrophoresis at 400 V for 45 minutes. Nopaline runs towards the cathode. The paper is then dried with a stream of hot air and drawn through phenanthrenequinone coloring agent (equal volume of 0.02% of phenanthrenequinone in ethanol and 10% of NaOH in 60% of ethanol) in the migration direction. The dried paper is viewed under longwave UV light and photographed. Arginine and arginine derivatives are stained a fluorescent yellow with the reagent.

Neomycin phosphotransferase (NPT II) enzyme test:

NPT II activity in plant tissue is detected as follows by in situ phosphorylation of kanamycin as described by Reiβ et al. (1984) and modified by Schreier et al. (1985). 50 mg of plant tissue are homogenised on ice in 50 µl of extraction buffer (10% of glycerol, 5% of 2-mercaptoethanol, 0.1% of SDS, 0.025% of bromophenol blue, 62.5 mM Tris pH 6.8), with addition of glass powder, and centrifuged for 10 minutes in an Eppendorf centrifuge at 4° C. 50 µl of the supernatant are applied to native polyacrylamide gel (145× 110×1.2 mm; separating gel: 10% of acrylamide, 0.33% of bisacrylamide, 0.375M Tris pH 8.8, collecting gel: 5% of acrylamide, 0.165% of bisacrylamide, 0.125M Tris pH 6.8) and subjected to electrophoresis overnight at 4° C. under 60 V. As soon as the bromophenol blue marker runs out of the gel, the gel is washed twice with distilled water for 10 minutes and once for 30 minutes with reaction buffer (67 mM Tris-maleate, pH 7.1, 42 mM $MgCl_2$, 400 mM ammonium chloride). The gel is placed on a glass plate of the same size and covered with a layer of 40 ml of 1% strength agarose in reaction buffer which contains the substrates kanamycin sulphate (20 µg/ml) and 20–200 µCi of $^{32}P$ ATP (Amersham). The sandwich gel is incubated for 30 minutes at room temperature and a sheet of phosphocellulose paper P81 (Whatman) is then laid over the agarose. Four layers of 3 MM filter paper, (Whatman) and a few paper handkerchiefs are stacked on top. The transfer of radioactive kanamycin phosphate phosphorylated in situ onto the P81 paper is stopped after 3–4 hours. The P81 paper is incubated for 30 minutes in a solution of proteinase K and 1% of sodium dodecyl sulphate (SDS) at 60° C. and then washed 3–4 times in 250 ml of 10 mM phosphate buffer pH 7.5 at 80° C., dried and autoradiographed for 1–12 hours at –70° C. (XAR5 film from Kodak).

4. Transformation of *Solanum tuberosum* (potato)

The transformation was transformed in exactly the manner described in EP-A-0,242,246, pages 14 to 15, the Agrobacteria containing Ti plasmids which carry pinosylvine synthase genes.

All the percentage data in the above examples relate to percentages by weight, unless stated otherwise.

The presence of the pinosylvine synthase genes in the plant cells and plants (tobacco) obtained according to the above examples was confirmed by Southern blot analysis. The expression of the pinosylvine synthase genes was detected by Northern blot analysis, and the pinosylvine synthase and pinosylvine were detected with the aid of specific antibodies. Transformed and non-transformed plants (for comparison) were sprayed with a spore suspension of Botrytis cinera and the fungal attack was rated after 1 week. The transformed plants showed an increased resistance to fungal attack (compared with the non-transformed comparison plants).

Hybridisation With the cDNA Sequence Contained in Plasmid Pin 5-49 or the cDNA Sequence According to SEQ ID No. 1

As mentioned above, the preferred pinosylvine synthase genes according to the invention are characterised in that they hybridise with the cDNA sequence contained in the plasmid pin 5-49 or its components or with the cDNA sequence according to SEQ ID No. 1 or its components and encode pinosylvine synthase. Moreover, the hybridisation can be generally used for the isolation and determination of pinosylvine synthase genes, e.g. in plants or plant parts.

Preferably phage clones containing pinosylvine synthase genes can be identified by hybridisation under low stringent conditions with pin 5-49 (or SEQ ID No. 1) resulting in a subpopulation of clones which can subsequently be identified as pinosylvine synthase genes clones, e.g. by direct gene transfer into plants (Hain et al 1985, 1990) and analysis of the transgenic plant tissue for enzymatic activity of pinosylvine synthase or the production of pinosylvine.

As an example pinosylvine synthase genes clones were identified using the cDNA clone 5-49 (or SEQ ID No. 1) as a probe under standard hybridisation conditions. Hybridisation was for 12 hours at 68° C. in standard buffer containing 2 SSC. Washes were performed at 74° C. in 2 SSC and 0.1%

SDS (2 times, 30 minutes), followed by one wash in 0.2 SSC, 0.1% SDS for 10 minutes. Phage clone DNA was cotransferred (with a plant selectable marker (kanamycin resistance) into tobacco protoplasts and found to direct the synthesis of pinoslyvine in tobacco.

Some of the media employed in the transformation of plants and plant cells are described below:

Am medium 3.5 g of $K_2HPO_4$ 1.5 g of $KH_2PO_4$ 0.5 g of $Na_3$ citrate 0.1 g of $MgSO_4 \times 7\ H_2O$ 1 g of $(NH_4)_2SO_4$ 2 g of glucose to 1 l Medium for Sterile Shoot Culture of Tobacco

| | | | |
|---|---|---|---|
| Macroelements | ½ of the concentration of the MS salts | | |
| Microelements | ½ of the concentration of the MS salts | | |
| Fe-EDTA | Murashige and Skoog (MS) | | |
| Myo-inositol | | | 100 mg/l |
| Sucrose | | | 10 mg/l |
| Agar | | | 8 g/l |
| Vitamins | Ca panthotenate | | 1 mg/l |
| | Biotin | | 10 mg/l |
| | Nicotinic acid | | 1 mg/l |
| | Pyridoxine | | 1 mg/l |
| | Thiamine | | 1 mg/l |
| pH 5.7 before autoclaving | | | |

K3 medium

For culture of *Nicotiana tabacum* petit Havana SR1, *Nicotiana tabacum* Wisconsin 38 and *Nicotiana plumbaginifolia* protoplasts (Nagy and Maliga, 1976)

| | | |
|---|---|---|
| Macroelements | $NH_4NO_3$ | 250 mg/l |
| | $KNO_3$ | 2500 mg/l |
| | $CaCl_2.2H_2O$ | 900 mg/l |
| | $MgSO_4.7H_2O$ | 250 mg/l |
| | $NaH_2PO_4.1H_2O$ | 150 mg/l |
| | $(NH_4)_2SO_4$ | 134 mg/l |
| | $CaHPO_4.1H_2O$ | 50 mg/l |
| Microelements | $H_3BO_3$ | 3 mg/l |
| | $MnSO_4.1H_2O$ | 10 mg/l |
| | $ZnSO_4.4H_2O$ | 2 mg/l |
| | KI | 0.75 mg/l |
| | $Na_2MoO_4.2H_2O$ | 0.25 mg/l |
| | $CuSO_4.5H_2O$ | 0.025 mg/l |
| | $CoCl_2.6H_2O$ | 0.025 mg/l |
| Fe-EDTA | $Na_2EDTA$ | 37.2 mg/l |
| | $FeSO_4.7H_2O$ | 27.8 mg/l |
| Inositol | | 100 mg/l |
| Sucrose | | 137 g/l |
| | | (= 0.4 M) |
| Xylose | | 250 mg/l |
| Vitamins | Nicotinic acid | 1 mg/l |
| | Pyridoxine | 1 mg/l |
| | Thiamine | 10 mg/l |
| Hormones | NAA | 1.0 mg/l |
| | Kinetin | 0.2 mg/l |
| pH 5.6 | | |
| Sterilise filter | | |

Linsmaier and Skoog Medium (Linsmaier and Skoog 1965)

For culture of regenerated protoplasts and for tissue culture of tobacco tumors and callus. Linsemaier and Skoog (LS) medium is Murashige and Skoog medium (Murashige and Skoog, 1962) with the following modifications:

thiamine is weighed in at a higher concentration of 0.4 mg/l instead of 0.1 mg/l;

glycine, pyridoxine and nicotinic acid are absent.

| | | |
|---|---|---|
| Macroelements | $NH_4NO_3$ | 1650 mg/l |
| | $KNO_3$ | 1900 mg/l |
| | $CaCl_2.2H_2O$ | 440 mg/l |
| | $MgSO_4.7H_2O$ | 370 mg/l |
| | $KH_2PO_4$ | 170 mg/l |
| Microelements | $H_3BO_3$ | 6.2 mg/l |
| | $MnSO_4.1H_2O$ | 22.3 mg/l |
| | $ZnSO_4.4H_2O$ | 8.6 mg/l |
| | KI | 0.83 mg/l |
| | $Na_2MoO_4.2H_2O$ | 0.25 mg/l |
| | $CuSO_4.5H_2O$ | 0.025 mg/l |
| | $CoCl_2.6H_2O$ | 0.025 mg/l |
| Fe-EDTA | $Na_2EDTA$ | 37.2 mg/l |
| | $FeSO_4.7H_2O$ | 27.8 mg/l |
| Inositol | | 100 mg/l |
| Sucrose | | 30 g/l |
| Agar | | 8 g/l |
| Vitamins | Thiamine | 0.4 mg/l |
| Hormones: | NAA | 1 mg/l |
| | Kinetin | 0.2 mg/l |
| pH 5.7 before autoclaving | | |

The following literature can be cited for transformation of plants and plant cells:

Aerts M., Jacobs M, Hernalsteens J. P., Van Montagu M., Schell J. (1983) Induction and in vitro culture of *Arabidopsis thaliana* crown gall rumours. Plant Sci Lett. 17:43–50

Fromm M. E., Taylor L. P., Walbot V. (1986) Stable transformation of maize after gene transfer by electroporation. Nature 319: 791–793

Gehlert, R., Schöppner, A., and Kindl, H. (1990) Synthase from Seedlings of *Pinus sylvestris*: Purification and Induction in Response to Fungal Infection. Molecular Plant-Microbe Interactions. Volume 3, No. 6, pages 444–449

Hain, R., Stable, P., Czernilofsky, A. Pp., Steinbiβ, H. H., Herrera-Estrella, L., Schell, J. (1985) Uptake, integration, expression and genetic transmission of a selectable chimeric gene by plant protoplasts. Molec Gen Genet 199:161–168

Herrera-Estrella L., De Block M., Messens E., Hernalsteens J. P., van Montagu M., Schell J. (1983) EMBO J. 2: 987–995.

Horsch R. B., Fry J. E., Hoffmann N. L., Eichholtz D., Rogers S. G., Fraley R. T. (1985) A simple and general method for transferring genes into plants. Scinece 277: 1229–1231

Krens F. H., Molendijk L., Wullems G. J., Schilperoort R. A. (1982) in vitro transformation of plant protoplasts with Ti-plasmid DNA, Nature 296:72–74

Koncz C., Schell J. (1986) The promoter of $T_L$-DNA gene 5 controls the tissue-specific expression of chimaeric genes carried by a noval type of Agrobacterium binary vector. Mol. Gen. Genet. (1986) 204: 338–396

Linsmaier D. M., Skoog F. (1965) Organic growth factor requirements of tobacco tissue cultures. Physiol plant 18:100–127

Marton L., Wullems G. J., Molendijk L., Schilperoort P. R. (1979) In vitro transformation of cultured cells from *Nicotiana tabacum* by *Agrobacterium tumefaciens*. Nature 277: 1229–131

Murashige, T. and Skoog F. (1962) A revised medium for rapid growth and bioassay with tobacco tissue culture. Physiol. Plant. 15, 47

Nagy J. I., Maliga P. (1976) Callus induction and plant regeneration from mesophyll protoplasts of *Nicotiana sylvestris*. Z Pflanzenphysiol 78:453–455

Otten L. A. B. M., Schilperoort R. A. (1978) A rapid microscale method for the detection of Lysopin and Nopalin dehydrogenase activities. Biochim biophys acta 527:497–500

Paszkowski J., Shillito R. D., Saul M., Mandak V., Hohn T., Hohn B., Potrykus I. (1984) Direct gene transfer to plants. EMBO J 3: 2717–2722

Shillito R. D., Paszkowski J. Potrykus I. (1983) Agarose plating and Bead type culture technique enable and stimulate deveeloopment of protoplast-derived colonies in an number of plant species. Pl Cell Rep 2:244–247

Van den Elzen P. J. M., Townsend J., Lee K. Y., Bedbrook J. R. (1985) Achimaeric resistance gene as a selectable marker in plant cells, Plant Mol. Biol. 5, 299–302.

Van Haute E., Joos H., Maes M., Warren G., Van Montagu M., Schell J. (1983) Intergenic transfer and exchange recombination of restriction fragments cloned in pBR322: a novel strategy for the reversed genetics of Ti plasmids of /Agrobacterium tumefaciens. EMBO J 2:411–418

Velten J., Velten L., Hain R., Schell J. (1984) Isolation of a dual plant promoter fragment from the Ti plasmid of Agrobacterium tumefaciens. EMBO J 12:2723–2730

Wullems G. J., Molendijk L., Ooms G., Schilperoort R. A. (1981) Differential expression of crown gall tumor markers in transformants obtained after in vitro Agrobacterium tumefaciens—induced transformation of cell wall regenerating protoplastss derived from Nicotiana tabacum. Proc Ntl Acad Sci 78:4344–4348

Zambryski P., Joos H., Genetello C., van Montagu M., Schell J. (1983) Ti-plasmid vector for the introduction of DNA into plant cells without altering their normal regeneration capacity, EMBO J 12: 2143–2150

Reiss B., Sprengel R., Will H. and Schaller H. (1984) A new sensitive method for qualitative and quantitative assay of neomycin phosphotransferase in crude cell tracts, GENE 1081: 211–217

Schreier P., Seftor E., Schell J. and Bohnert H. (1985) The use of nuclear-encoded sequences to direct the light-regulated synthesis and transport of a foreingn protein into plant chloroplasts, EMBO J Volume 4, No. 1:25–32

The following published patent applications may furthermore be mentioned:

EP-A 116,718
EP-A 159,418
EP-A 120,515
EP-A-120,516
EP-A-172,112
EP-A-140,556
EP-A-174,166
EP-A-122,791
EP-A-126,546
EP-A-164,597
EP-A-175,966
WO 84/02913
WO 84/02919
WO 84/02920

What is claimed is:

1. A transformed plant cell containing within its genome a nucleotide sequence selected from the group consisting of (i) the nucleotide sequence of the cDNA contained in plasmid pin 5-49, (ii) the nucleotide sequence of the cDNA sequence of SEQ ID No: 1 and (iii) the nucleotide sequence of a degenerate variant of (i) or (ii), wherein said nucleotide sequence is expressed when said transformed plant cell is exposed to fungi, said transformed plant cell having increased resistance to said fungi as compared to an untransformed plant cell of the same cell type and plant species exposed to the same fungi under the same conditions, and said increased resistance to said fungi being a result of the expression of said nucleotide sequence.

2. A transformed plant part containing within its genome a nucleotide sequence selected from the group consisting of (i) the nucleotide sequence of the cDNA contained in plasmid pin 5-49, (ii) the nucleotide sequence of the cDNA sequence of SEQ ID No: 1 and (iii) the nucleotide sequence of a degenerate variant of (i) or (ii), wherein said nucleotide sequence is expressed when said transformed plant part is exposed to fungi, said transformed plant part having increased resistance to said fungi as compared to an untransformed plant part of the same plant part type and plant species exposed to the same fungi under the same conditions, and said increased resistance to said fungi being a result of the expression of said nucleotide sequence.

3. A transformed whole plant containing within its genome a nucleotide sequence selected from the group consisting of (i) the nucleotide sequence of the cDNA contained in plasmid pin 5-49, (ii) the nucleotide sequence of the cDNA sequence of SEQ ID No: 1 and (iii) the nucleotide sequence of a degenerate variant of (i) or (ii), wherein said nucleotide sequence is expressed when said transformed whole plant is exposed to fungi, said transformed whole plant having increased resistance to said fungi as compared to an untransformed whole plant of the same plant species exposed to the same fungi under the same conditions, and said increased resistance to said fungi being a result of the expression of said nucleotide sequence.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 570 nucleotides
        ( B ) TYPE: Nucleic acid
        ( C ) STRANDEDNESS: Single
        ( D ) TOPOLOGY: Linear ( i i ) MOLECULE TYPE: cDNA from mRNA ( v i ) ORIGINAL SOURCE:
        ( A ) ORGANISM: Pinus sylvestris ( x i ) SEQUENCE DESCRIPTION: SEQ ID NO:1:

```
AAG  AAT  CCC  GAT  GTG  TGC  GCG  TTC  GTG  GAG  GTG  CCA  TCG              39
Lys  Asn  Pro  Asp  Val  Cys  Ala  Phe  Val  Glu  Val  Pro  Ser
 1                   5                        10

TTG  GAC  GCA  CGG  CAG  GCC  ATG  TTG  GCT  ATG  GAG  GTG  CCC              78
Leu  Asp  Ala  Arg  Gln  Ala  Met  Leu  Ala  Met  Glu  Val  Pro
     15                        20                       25

CGG  CTG  GCA  AAA  GAG  GCC  GCT  GAA  AAG  GCC  ATT  CAG  GAG             117
Arg  Leu  Ala  Lys  Glu  Ala  Ala  Glu  Lys  Ala  Ile  Gln  Glu
               30                       35

TGG  GGG  CAG  TCC  AAG  TCT  GGG  ATC  ACT  CAT  CTC  ATA  TTT             156
Trp  Gly  Gln  Ser  Lys  Ser  Gly  Ile  Thr  His  Leu  Ile  Phe
 40                      45                  50

TGC  AGC  ACA  ACG  ACT  CCG  GAT  CTA  CCT  GGA  GCA  GAC  TTT             195
Cys  Ser  Thr  Thr  Thr  Pro  Asp  Leu  Pro  Gly  Ala  Asp  Phe
          55                        60                       65

GAG  GTA  GCC  AAG  TTG  CTG  GGG  CTG  CAC  CCG  AGT  GTG  AAG             234
Glu  Val  Ala  Lys  Leu  Leu  Gly  Leu  His  Pro  Ser  Val  Lys
```

|     |     |     |     |     |     | 70  |     |     |     |     | 75  |     |     |     |
|-----|-----|-----|-----|-----|-----|-----|-----|-----|-----|-----|-----|-----|-----|-----|
| AGA | GTG | GGC | GTG | TTC | CAA | CAT | GGC | TGC | TTC | GCC | GGA | GGC |     | 273 |
| Arg | Val 80 | Gly | Val | Phe | Gln | His 85 | Gly | Cys | Phe | Ala | Gly 90 | Gly |     |     |
| ACC | GTT | CTT | CGA | ATG | GCG | AAA | GAC | CTT | GCC | GAA | AAC | AAT |     | 312 |
| Thr | Val | Leu | Arg 95 | Met | Ala | Lys | Asp | Leu 100 | Ala | Glu | Asn | Asn |     |     |
| CGA | GGA | GCT | CGG | GTG | CTG | GTC | ATC | TGT | AGT | GAA | ACC | ACC |     | 351 |
| Arg 105 | Gly | Ala | Arg | Val | Leu 110 | Val | Ile | Cys | Ser | Glu 115 | Thr | Thr |     |     |
| GCC | GTT | ACC | TTT | CGT | GGA | CCC | TCC | GAG | ACT | CAC | CTG | GAC |     | 390 |
| Ala | Val | Thr 120 | Phe | Arg | Gly | Pro | Ser 125 | Glu | Thr | His | Leu | Asp 130 |     |     |
| AGC | CTG | GTG | GGG | CAA | GCT | CTG | TTT | GGC | GAC | GGT | GCT | TCT |     | 429 |
| Ser | Leu | Val | Gly | Gln 135 | Ala | Leu | Phe | Gly | Asp 140 | Gly | Ala | Ser |     |     |
| GCC | CTC | ATC | GTG | GGA | GCT | GAT | CCC | ATC | CCT | CAA | GTG | GAG |     | 468 |
| Ala | Leu 145 | Ile | Val | Gly | Ala | Asp 150 | Pro | Ile | Pro | Gln | Val 155 | Glu |     |     |
| AAG | GCC | TGT | TTC | GAA | ATC | GTT | TGG | ACA | GCC | CAG | ACA | GTT |     | 507 |
| Lys | Ala | Cys | Phe 160 | Glu | Ile | Val | Trp | Thr 165 | Ala | Gln | Thr | Val |     |     |
| GTT | CCC | AAC | AGC | GAG | GGA | GCC | ATC | GGT | GGG | AAG | GTG | AGA |     | 546 |
| Val 170 | Pro | Asn | Ser | Glu | Gly 175 | Ala | Ile | Gly | Gly | Lys 180 | Val | Arg |     |     |
| GAG | GTC | GGG | CTG | ACC | TTC | CAA | CTC |     |     |     |     |     |     | 570 |
| Glu | Val | Gly 185 | Leu | Thr | Phe | Gln | Leu 190 |     |     |     |     |     |     |     |